US00PP13004P2

(12) United States Plant Patent
Hanes

(10) Patent No.: US PP13,004 P2
(45) Date of Patent: Sep. 24, 2002

(54) GERANIUM PLANT NAMED 'CLIPS RED II'

(75) Inventor: Mitchell Eugene Hanes, Morgan Hill, CA (US)

(73) Assignee: Goldsmith Plants, Inc., Gilroy, CA (US)

( * ) Notice: Subject to any disclaimer, the term of this patent is extended or adjusted under 35 U.S.C. 154(b) by 0 days.

(21) Appl. No.: 09/802,868

(22) Filed: Mar. 12, 2001

(51) Int. Cl.[7] ..... A01H 5/00
(52) U.S. Cl. ..... Plt./330
(58) Field of Search ..... Plt./330, 324, 325

*Primary Examiner*—Bruce R. Campell
*Assistant Examiner*—June Hwu
(74) *Attorney, Agent, or Firm*—Rothwell, Figg, Ernst & Manbeck

(57) ABSTRACT

A geranium cultivar particularly distinguished by dark green foliage, red flower color, and semi-double flowers on large umbels, fast rooting and exhibits vigorous growth.

1 Drawing Sheet

GENUS AND SPECIES

*Pelargonium hortorum.*

VARIETY DENOMINATION

Figure 1:
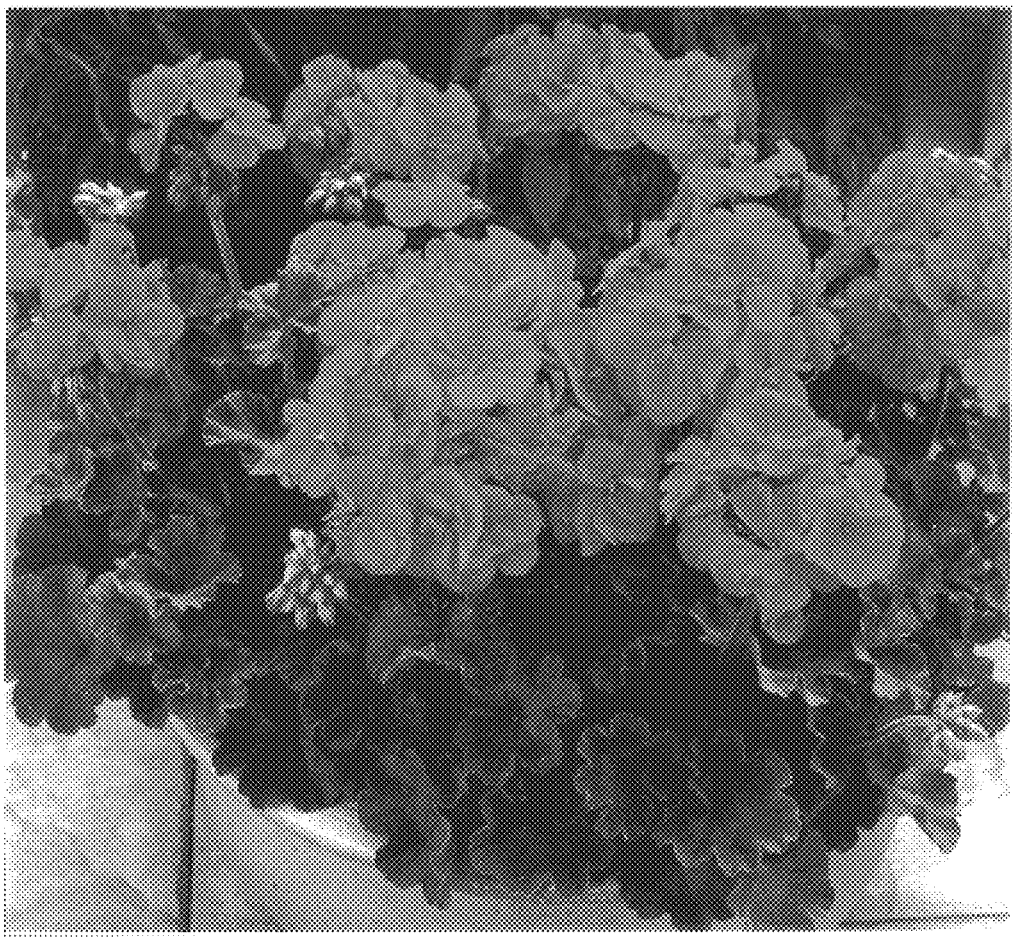

'Clips Red II'.

BACKGROUND OF THE NEW PLANT

The present invention comprises a new and distinct cultivar of geranium, botanically known as *Pelargonium hortorum* Bailey, and hereinafter referred to by the cultivar name 'Clips Red II'. The new cultivar is propagated from a seedling resulting from the cross of an unnamed and unpatented proprietary line known as 7108-1 which is a red single flowered geranium and an unnamed and unpatented proprietary line known as 6087-4 which is a red semi-double geranium flower.

'Clips Red II 'is a product of a planned breeding program intended to create new geranium cultivars with red colored flowers, semi-double flower form, dark green foliage, vigorous growth and superior cutting productivity.

The new cultivar was created in 1997 in Gilroy, Calif. and has been repeatedly asexually reproduced by cuttings in Gilroy, Calif. and Guatemala over a three year period. It has also been trialed at Gilroy, Calif. and Andijk, The Netherlands. It has been found to retain its distinctive characteristics through successive propagations; and this novelty is firmly fixed.

DESCRIPTION OF PHOTOGRAPH

This new geranium plant is illustrated by the accompanying photograph which shows blooms, buds, and foliage of the plant in full color, the colors shown being as true as can be reasonably obtained by conventional photographic procedures.

FIG. 1 shows overall plant habit.

DESCRIPTION OF THE NEW CULTIVAR

The following detailed descriptions set forth the distinctive characteristics of 'Clips Red II'. The data which defines these characteristics were collected from asexual reproductions carried out in Gilroy, Calif. The plant history was taken on five month old plants grown in 8 inch pots, blossomed under natural light in a greenhouse and color reading were taken in the greenhouse in Gilroy, Calif. Color references are primarily to The R.H.S. Colour Chart of The Royal Horticultural Society of London (R.H.S.).

DETAILED BOTANICAL DESCRIPTION

Classification:
*Botanical.*—*Pelargonium hortorum* Bailey.
*Commercial.*—Geranium.
Form: Upright, rounded.
Height:
*From soil level to top of plant* (*excluding blooms*).—17 cm.
*From soil level to top of umbels.*—30–34 cm.
Width: 30–32.5 cm.
Time to produce a finished flowering plant: 12 weeks.
Outdoor plant performance: Good heat tolerance, strong growth, maintains rounded habit.
Time to initiate roots: 9–10 days.
Time to develop roots: 27 days.
Root description: White, slightly pubescent, fibrous yet coarse.

The Leaves

Length: 4.5–6.5 cm.
Width: 7.5–9.0 cm depending on age.
Apex measurement: 3.5–5.0 cm.
Base measurement: 6.0–6.5 cm.
Shape: Reniform.
Margin: Crenate.
Texture: Leathery and pubescent on both surfaces.
Ribs and veins: Palmate (digitate), 3.5–4.0 cm long.
Color:
*Upper side.*—Yellow-green RHS 147A with a darker brown zone in the center of the leaf of RHS 200A over RHS 147A.
*Under side.*—Yellow-green RHS 147B.
*Ribs.*—Yellow-green RHS 147B.
*Veins.*—Yellow-green RHS 147B.
Petiole length: 6.2–7.0 cm depending on age of the leaf.
Petiole diameter: 3.0 mm.
Petiole color: Yellow-green RHS 147B.
Lateral branch length: 3.0–7.0 cm.

Internode length: 1.0–2.5 cm.
Lateral branch color: Yellow-green RHS 146B.

The Bud

Diameter: 6 mm.
Length: 9 mm.
Shape: Elliptic.
Color when sepals first divide: Red RHS 45B.
Number of sepals: 5.
Length of sepals: 8–9 mm.
Width of sepals: 3 mm.
Apex shape: Cuspidate.
Base shape: Truncate
Sepal color in an open flower: Upper is green RHS 143C with thin stripes of dark red RHS 183C running lengthwise towards apex, the base is dark red RHS 183B; Lower is green RHS 143C.

The Flower

Bloom season: Continuous throughout the year in greenhouse or Zone 9 climate.
Size: Approximately 5 cm in diameter.
Form: Polypetalous, cup shaped, later flattening to shallow cup shape.
Petals/petaloids: 6–7 imbricate petals, 2–3 petaloids; Shape: spatulate.
Apex shape: Obtuse.
Base shape: Attenuate.
Margin: Entire, slightly undulating.
Petal color:
*Upper surface.*—Red RHS 44B.
*Lower surface.*—Red RHS 40A.
Surface texture of petals and petaloids: Papillose (satiny).
Petaloid color:
*Upper.*—Red RHS 44B.
*Lower.*—Red RHS 40A.
Color change with age: Minimal.
Pedicel length: Approximately 2–2.7 cm.
Pedicel color: Greyed-purple RHS 183B.
Flower persistence: An open flower will hold it's petals until the flower begins to dehisce, or approximately 7–10 days.

The Inflorescence

Type: An umbel composed of approximately 23–25 flowers.
Diameter: 8.5–9.0 cm.
Depth: 6.0 cm.
Peduncle length: 11.0–19.0 cm.
Peduncle color: Yellow-green RHS 146B with areas of greyed-purple RHS 183B on portions that are directly exposed to sunlight; texture is pubescent with small white hairs.

The Reproductive Organs

Anthers: 5–6, 2 of which are fused to petaloids.
Anther color: Red RHS 51B prior to anthesis.
Filament color: Apex is Red RHS 51B; Base is White RHS 155A.
Lengths of anthers and filaments: Anthers — 0.2 cm; filament 0.7–0.9 cm.
Pollen amount and color: Moderate orange RHS 26A.
Pistil: 1 with a length of 1 cm.
Stigma: 5 linear lobes with a color of red RHS 51B.
Style: 2 mm with a color of red RHS 51B.
Ovary: At anthesis, densely pubescent with white hairs, oblong, green drying to a light brown at maturity.
Seed number: Maximum of 5 per spike.
Seed length: 4–5 mm.
Seed width: 1.5–2.0 mm.
Seed color: Brown RHS 165A, may darken with age.

Disease and Insect Resistance

No susceptibility to diseases or insects noted to date.

Comparison with Known Cultivars

'Clips Red II' has darker foliage and semi-double flower form versus a single flower form for 7108-1. When compared to 6087-4, 'Clips Red II' has darker foliage and is earlier flowering.

I claim:

1. A new and distinct cultivar of geranium plant as shown and described herein.

* * * * *